United States Patent
Arnold et al.

(10) Patent No.: US 10,103,015 B2
(45) Date of Patent: Oct. 16, 2018

(54) SAMPLING INTERFACE FOR MASS SPECTROMETRY SYSTEMS AND METHODS

(71) Applicants: DH Technologies Development PTE Ltd., Singapore (SG); German Augusto Gomez Rios, Waterloo (CA); Janusz B. Pawliszyn, Waterloo (CA)

(72) Inventors: Don W. Arnold, Livermore, CA (US); Thomas R. Covey, Newmarket (CA); German Augusto Gomez Rios, Waterloo (CA); Chang Liu, Richmond Hill (CA); Janusz B. Pawliszyn, Waterloo (CA)

(73) Assignees: DH Technologies Development Pte. Ltd., Singapore (SG); Janusz Pawliszyn, Ontario (CA); German Augusto Gomez Rios, Ontario (CA)

( * ) Notice: Subject to any disclaimer, the term of this patent is extended or adjusted under 35 U.S.C. 154(b) by 0 days.

(21) Appl. No.: 15/581,172

(22) Filed: Apr. 28, 2017

(65) Prior Publication Data
US 2017/0316926 A1 Nov. 2, 2017

Related U.S. Application Data

(60) Provisional application No. 62/329,870, filed on Apr. 29, 2016.

(51) Int. Cl.
*H01J 49/00* (2006.01)
*H01J 49/04* (2006.01)

(52) U.S. Cl.
CPC ...... *H01J 49/0404* (2013.01); *H01J 49/0031* (2013.01); *H01J 49/0459* (2013.01)

(58) Field of Classification Search
CPC . H01J 49/0404; H01J 49/0031; H01J 49/0459
(Continued)

(56) References Cited

U.S. PATENT DOCUMENTS

| 5,691,206 A | 11/1997 | Pawliszyn |
| 2012/0053065 A1* | 3/2012 | Van Berkel ......... H01J 49/0431 506/7 |

(Continued)

FOREIGN PATENT DOCUMENTS

WO 2015188282 12/2015

OTHER PUBLICATIONS

Gary J. Van Berkel et al. "An open port sampling interface for liquid introduction atmospheric pressure ionization mass spectrometry", Rapid Communications in Mass Spectrometry, 2015, 29, pp. 1749-1756.

*Primary Examiner* — Michael Maskell (57) ABSTRACT

Methods and systems for delivering a liquid sample to an ion source for the generation of ions and subsequent analysis by mass spectrometry are provided herein. In accordance with various aspects of the present teachings, MS-based systems and methods are provided in which a desorption solvent utilized in a sampling interface to desorb one or more analyte species from an SPME device is fluidly coupled to an ion source for ionizing the one or more analyte species desorbed into the desorption solvent for subsequent mass spectrometric analysis (e.g., without a liquid chromatography (LC) column between the sampling interface and the ion source). In accordance with various aspects of the methods and systems described herein, the configuration the sampling interface can be optimized so as to reduce the fluid volume dead space about the fluid inlet so as to concentrate the one or more analyte species desorbed at optimized conditions from the SPME substrate in a decreased volume of the desorption solvent when the SPME device is inserted into sampling interface.

18 Claims, 7 Drawing Sheets

(58) Field of Classification Search
USPC .................................... 250/281, 282, 288
See application file for complete search history.

(56) References Cited

U.S. PATENT DOCUMENTS

| | | |
|---|---|---|
| 2012/0079894 A1 | 4/2012 | Van Berkel |
| 2012/0085900 A1* | 4/2012 | Verbeck, IV ....... H01J 49/0459 250/282 |
| 2013/0214154 A1* | 8/2013 | McEwen ............. H01J 49/0404 250/288 |
| 2015/0260684 A1* | 9/2015 | Blanksby ............. G01N 27/622 250/288 |
| 2016/0299109 A1 | 10/2016 | Van Berkel |

* cited by examiner

- Blank

MRM³ 286.1/204.1/169.1 for d9-clenbuterol    MRM³ 277.1/203.1/168.1 for clenbuterol

- 0.1 ng/mL clenbuterol + 10 ng/mL d9-clenbuterol

MRM³ 286.1/204.1/169.1 for d9-clenbuterol    MRM³ 277.1/203.1/168.1 for clenbuterol

SAMPLING INTERFACE FOR MASS SPECTROMETRY SYSTEMS AND METHODS

RELATED APPLICATIONS

This application claims the benefit of priority from U.S. Provisional Application Ser. No. 62/329,870, filed on Apr. 29, 2016, the entire contents of which is incorporated by reference herein.

FIELD

The present teachings generally relate to mass spectrometry, and more particularly to sampling interfaces for mass spectrometry systems and methods.

INTRODUCTION

Mass spectrometry (MS) is an analytical technique for determining the elemental composition of test substances with both qualitative and quantitative applications. MS can be useful for identifying unknown compounds, determining the isotopic composition of elements in a molecule, determining the structure of a particular compound by observing its fragmentation, and quantifying the amount of a particular compound in a sample. Given its sensitivity and selectivity, MS is particularly important in life science applications.

In the analysis of complex sample matrices (e.g., biological, environmental, and food samples), many current MS techniques require extensive pre-treatment steps to be performed on the sample prior to MS detection/analysis of the analyte of interest. Such pre-analytical steps can include sampling (i.e., sample collection) and sample preparation (separation from the matrix, concentration, fractionation and, if necessary, derivatization). It has been estimated, for example, that more than 80% of the overall analytical process can be spent on sample collection and preparation in order to enable the analyte's detection via MS or to remove potential sources of interference contained within the sample matrix, while nonetheless increasing potential sources of dilution and/or error at each sample preparation stage.

Ideally, sample preparation techniques for MS should be fast, reliable, reproducible, inexpensive, and in some aspects, amenable to automation. One recent example of an improved sample preparation technique is solid-phase microextraction (SPME), which essentially integrates sampling, sample preparation, and extraction into a single solvent-free step. Generally, SPME devices utilize a fiber or other surface (e.g., blades, micro-tips, pins, or mesh) coated with an extracting phase to which analytes within the sample can be preferentially adsorbed when the device is inserted into the sample. Because extraction can take place in situ by inserting a biocompatible device directly into tissue, blood, or other biological matrix for a short period of time, SPME does not require any sample collection. Alternatively, SPME devices can be used for ex vivo analysis using a small amount of a collected sample (i.e., a sample aliquot).

Though SPME is generally considered to be accurate and simple and can result in decreased sample preparation time and disposal costs, the mass-spectrometric based analysis of SPME-prepared samples may nonetheless require additional equipment and/or time-consuming steps in order to ionize the analyte from the SPME device directly or to desorb the analytes from the SPME device prior to ionization as required for mass spectrometry (MS). By way of example, various ionization methods have been developed that can desorb/ionize analytes from condensed-phase samples with minimal sample handling (e.g., desorption electrospray ionization (DESI) and direct analysis in real time (DART), which "wipe-off" analytes from the samples by exposing their surfaces to an ionizing medium such as a gas or an aerosol). However, such techniques can also require sophisticated and costly equipment.

Alternatively, additional desorption steps have been utilized to extract the analytes from the SPME device prior to ionization via ionization techniques other than DESI or DART. For example, because electrospray ionization (ESI) is one of the most common ionization methods and requires the analyte to be in solution, some users have utilized liquid desorption and subsequent purification/separation of the extracted/enriched analytes via high-performance liquid chromatography (HPLC) prior to MS analysis. However, liquid desorption prior to HPLC may require several minutes to transfer the analyte from the SPME coating to the liquid phase due to requirements imposed on the HPLC mobile phase (weak solvent strength). Moreover, as discussed above, these increased sample-preparation/separation steps can decrease throughput, introduce potential sources of error, increase dilution, and cannot be easily automated. Alternatively, some groups have proposed substantial modifications to the standard electrospray ion source. Typically in ESI, a liquid sample is continuously discharged into an ionization chamber from within an electrically conductive capillary, while an electric potential difference between the capillary and a counter electrode generates a strong electric field within the ionization chamber that electrically charges the liquid sample. This electric field causes the liquid discharged from the capillary to disperse into a plurality of charged micro-droplets drawn toward the counter electrode if the charge imposed on the liquid's surface is strong enough to overcome the surface tension of the liquid (i.e., the particles attempt to disperse the charge and return to a lower energy state). As solvent within the micro-droplets evaporates during desolvation in the ionization chamber, charged analyte ions can then enter a sampling orifice of the counter electrode for subsequent mass spectrometric analysis. PCT Pub. No. WO2015188282 entitled "A Probe For Extraction Of Molecules Of Interest From A Sample," which is incorporated by reference herein in its entirety, for example, thus purports to provide for electrospray ionization from an SPME device by applying the ionizing electric potential to the conductive SPME device itself (to which a discrete amount of a desorption solution is applied) such that ions are generated directly from the edges of the wetted substrate.

There remains a need for improved and/or reduced-cost systems that enable fast-coupling of SPME devices to MS systems with minimal alterations to the front-end while maintaining sensitivity, simplicity, selectivity, speed and throughput.

SUMMARY

Methods and systems for delivering a liquid sample to an ion source for the generation of ions and subsequent analysis by mass spectrometry are provided herein. In accordance with various aspects of the present teachings, MS-based systems and methods are provided in which a desorption solvent utilized in a sampling interface to desorb one or more analyte species from an SPME device is fluidly coupled to an ion source for ionizing the one or more analyte species desorbed into the desorption solvent for subsequent mass spectrometric analysis (e.g., without a liquid chromatography (LC) column between the sampling interface and the ion source). In accordance with various aspects of the methods and systems described herein, the configuration of the sampling interface can be optimized so as to reduce the fluid volume dead space about the fluid inlet and the SPME device so as to concentrate the one or more analyte species desorbed from the SPME device in a decreased volume of the desorption solvent when the SPME device is inserted into sampling interface. In some aspects, for example, the SPME device-receiving port of the substrate sampling probe (e.g., an open port probe) can be configured, and in some aspects, such that the SPME substrate occupies at least 20 percent of the fluid volume in the SPME device-receiving port (i.e., less than 80% of the volume of the SPME device-receiving port is occupied by desorption solvent).

In accordance with various exemplary aspects of the present teachings, a method for performing chemical analysis is provided, the method comprising inserting at least a portion of a SPME substrate into an open end of a substrate sampling probe (e.g., an open port probe), the SPME substrate having a surface coated with an extraction phase to which one or more analyte species are adsorbed, wherein inserting said SPME substrate comprises placing the coated surface having said one or more analytes species adsorbed thereto within a fluid pathway extending from a desorption solvent source to an ion source probe of an ion source. The method also comprises flowing a desorption solvent through the fluid pathway such that at least a portion of the one or more analyte species is desorbed from the coated surface and is delivered to the ion source probe along the fluid pathway within the desorption solvent. The desorption solvent containing the portion of the one or more analyte species can then be discharged from the ion source probe (e.g., into an ionization chamber) so as to form one or more ionized analyte species and mass spectrometric analysis can be performed on the one or more ionized analyte species.

In accordance with some aspects of the present teachings, the substrate sampling probe can comprise an outer tube (e.g., a capillary tube) extending from a proximal end to a distal end and an inner tube (e.g., a capillary tube) extending from a proximal end to a distal end and disposed within said outer capillary tube, wherein the distal end of the inner capillary tube is recessed relative to the distal end of the outer capillary tube so as to define a distal fluid chamber between the distal end of the inner capillary tube and the distal, open end of the outer capillary tube. Moreover, the inner and outer capillary tubes can define a desorption solvent conduit and a sampling conduit in fluid communication with one another via the distal fluid chamber, the desorption solvent conduit extending from an inlet end fluidly coupled to the desorption solvent source to an outlet end in fluid communication with the distal fluid chamber, and the sampling conduit extending from an inlet end in fluid communication with the distal fluid chamber to an outlet end fluidly coupled to the ion source probe. In some related aspects, inserting the portion of a SPME substrate into the open end of the substrate sampling probe can comprise disposing the SPME substrate in the distal fluid chamber such that the SPME substrate occupies at least 20 percent (e.g., at least 30%, at least 40%, at least 50%, at least 60%, at least 70%, at least 80%, at least 90%) of the distal fluid chamber.

In various aspects, the method can further comprise one or more steps including, for example, conditioning the SPME substrate prior to insertion in a sample, inserting the SPME substrate into a sample so as to adsorb one or more analyte species contained within the sample to the coated surface, extracting the one or more analyte species from the sample, and rinsing the SPME substrate (e.g., with water) prior to inserting the SPME substrate into the substrate sampling probe. In some related aspects, after the one or more analytes species are adsorbed to the coated surface, the SPME substrate is inserted into the substrate sampling probe without a step of performing liquid chromatography. In accordance with various aspects of the present teachings, one or more of the above steps can be automated (e.g., performed by a robotic system).

In accordance with various aspects of the present teachings, a system for performing chemical analysis is provided, the system comprising a substrate having a surface coated with an extraction phase configured to adsorb one or more species of analyte (e.g., a SPME substrate) and a substrate sampling probe. In exemplary aspects, the substrate sampling probe can comprise an outer capillary tube extending from a proximal end to a distal end and an inner capillary tube extending from a proximal end to a distal end and disposed within said outer capillary tube, wherein said distal end of the inner capillary tube is recessed relative to the distal end of the outer capillary tube so as to define a distal fluid chamber between the distal end of the inner capillary tube and the distal end of the outer capillary tube. The inner and outer capillary tubes can define a desorption solvent conduit and a sampling conduit in fluid communication with one another via the distal fluid chamber, the desorption solvent conduit extending from an inlet end configured to fluidly couple to a desorption solvent source to an outlet end in fluid communication with the distal fluid chamber, and the sampling conduit extending from an inlet end in fluid communication with the distal fluid chamber to an outlet end configured to fluidly couple to an ion source probe for discharging desorption solvent received at the inlet end of the sampling conduit into an ionization chamber in fluid communication with a sampling orifice of a mass spectrometer. At least a portion of the substrate comprising the coated surface can be configured to be inserted through the distal end of the outer capillary tube such that the coated surface having the analyte species adsorbed thereto is in contact with the desorption solvent as the desorption solvent flows from the desorption solvent conduit into the sampling conduit through the distal fluid chamber. In various aspects, the substrate comprising the coated surface can be configured to be inserted through the distal end of the outer capillary tube such that said substrate occupies at least 20 percent (e.g., at least 50%, at least 80%) of the distal fluid chamber.

In various related aspects, the system can further comprise a desorption solvent source fluidly coupled to the inlet end of the desorption solvent conduit and a pump mechanism for delivering the desorption solvent from the desorption solvent source to the inlet end of the desorption solvent conduit. In some related aspects, the system can further comprise a controller for adjusting a fluid flow rate of the desorption solvent flowing through one or more of the desorption solvent conduit, the sampling conduit, and the ion source probe. Additionally or alternatively, the system can further comprise an ion source probe, an ionization chamber, and a mass spectrometer system, wherein the ion source probe is in fluid communication with the outlet end of the sampling conduit and comprises a distal end disposed in the ionization chamber, wherein analytes contained within said desorption solvent are configured to ionize as the desorption solvent is discharged into the ionization chamber.

In certain aspects, the system can also include a specimen holder configured to support the substrate during insertion into the substrate sampling probe. An actuation mechanism coupled to the specimen holder can be configured to insert the substrate into the distal end of the outer capillary tube such that the coated surface of said substrate is in contact with the desorption solvent. In such a manner, various steps of the chemical analysis procedures performed by the exemplary systems described herein can be automated (e.g., performed by a robotic system). In some aspects, for example, the system can comprise a specimen stage configured to support a plurality of substrates, wherein the actuation mechanism is configured to sequentially insert each of said plurality of substrates into the distal end of the outer capillary tube. In some related aspects, though the desorption process and MS-sampling may be performed sequentially, the actuation mechanism can be configured to pre-treat a plurality of substrates simultaneously to increase throughput (e.g., pre-conditioning of the SPME substrate, sampling, and rinsing steps).

In accordance with various aspects of the present teachings, systems for analyzing a chemical composition of a specimen are provided comprising a substrate sampling probe configured to be directly coupled to an ion source of a mass spectrometer system. In certain aspects, the substrate sampling probe can comprise an outer tube (e.g., a capillary tube) extending from a proximal end to a distal end; and an inner tube (e.g., a capillary tube) extending from a proximal end to a distal end and disposed within said outer capillary tube, wherein the distal end of the inner capillary tube is recessed relative to the distal end of the outer capillary tube so as to define a distal fluid chamber between the distal end of the inner capillary tube and the distal end of the outer capillary tube. The inner and outer capillary tubes can also define a desorption solvent conduit and a sampling conduit in fluid communication with one another via the distal fluid chamber, the desorption solvent conduit extending from an inlet end configured to fluidly couple to a desorption solvent source to an outlet end in fluid communication with the distal fluid chamber; the sampling conduit extending from an inlet end in fluid communication with said distal fluid chamber to an outlet end configured to fluidly couple to an ion source probe for discharging desorption solvent received at the inlet end of the sampling conduit into an ionization chamber in fluid communication with a sampling orifice of a mass spectrometer. The distal end of the outer capillary tube can be configured to receive at least a portion of a substrate comprising a coated surface having one or more analyte species adsorbed thereto (e.g., a SPME substrate) such that the coated surface is in contact with the desorption solvent as the desorption solvent flows from the desorption solvent conduit into the sampling conduit through the distal fluid chamber. In various aspects, the substrate can occupy at least 20 percent (e.g., at least 50%, at least 80%) of the distal fluid chamber when the substrate is inserted into the distal end of the outer capillary tube. In various aspects, the inner and outer capillary tubes can be coaxial.

In some aspects of the above system, the cross-sectional area of at least a portion of the distal fluid chamber can be less than an internal cross-sectional area of a proximal portion of the outer capillary tube. In related aspects, for example, a portion of the inner sidewall of the outer capillary tube adjacent the distal fluid chamber can extend inwardly (e.g., toward the longitudinal axis of the outer capillary tube) or alternatively the system can comprise a plug configured to be coupled to the distal end of the outer capillary tube so as to reduce the volume of the distal fluid chamber. In some aspects, when the substrate comprises a SPME blade, for example, at least a portion of the reduced cross-section distal fluid chamber can comprise opposed planar surfaces that are separated by a distance just greater than the thickness of the blade. In some other aspects, the cross-sectional area of a portion of the distal fluid chamber can be larger than an internal cross-sectional area of a proximal portion of the outer capillary tube, so as to enable the outer capillary tube to receive an SPME device having a dimension larger in at least one axis relative the diameter of the proximal portion of the outer capillary tube (e.g., an SPME blade having a width greater than about 2 mm).

In some aspects, an axial bore of the inner capillary tube defines the sampling conduit and a space between the inner capillary tube and the outer capillary tube defines the desorption solvent conduit. Alternatively, the axial bore of the inner capillary tube can define the desorption solvent conduit and the space between the inner capillary tube and the outer capillary tube can define the sampling conduit.

These and other features of the applicant's teachings are set forth herein.

BRIEF DESCRIPTION OF THE DRAWINGS

The skilled person in the art will understand that the drawings, described below, are for illustration purposes only. The drawings are not intended to limit the scope of the applicant's teachings in any way.

DETAILED DESCRIPTION

It will be appreciated that for clarity, the following discussion will explicate various aspects of embodiments of the applicant's teachings, while omitting certain specific details wherever convenient or appropriate to do so. For example, discussion of like or analogous features in alternative embodiments may be somewhat abbreviated. Well-known ideas or concepts may also for brevity not be discussed in any great detail. The skilled person will recognize that some embodiments of the applicant's teachings may not require certain of the specifically described details in every implementation, which are set forth herein only to provide a thorough understanding of the embodiments. Similarly it will be apparent that the described embodiments may be susceptible to alteration or variation according to common general knowledge without departing from the scope of the disclosure. The following detailed description of embodiments is not to be regarded as limiting the scope of the applicant's teachings in any manner.

In accordance with various aspects of the applicant's teachings, MS-based analytical systems and methods are provided herein in which a desorption solvent utilized in a sampling interface to desorb one or more analyte species from an SPME device is fluidly coupled to an ion source for ionizing the one or more analyte species desorbed into the desorption solvent for subsequent mass spectrometric analysis (e.g., without a liquid chromatography (LC) column between the sampling interface and the ion source). Whereas current methods for ionizing liquid samples derived from SPME devices often utilize complex sample preparation steps in which SPME-extracted analytes are first desorbed from the SPME device and subsequently subject to additional sample processing steps (e.g., concentration/purification via LC) that are not amenable to automation prior to ionization/mass spectrometric analysis, systems and methods in accordance with various aspects of the present teachings provide a simplified workflow in which the SPME devices having one or more analytes adsorbed thereon can be coupled directly to the ion source of an MS system. In various aspects, the systems and methods described herein can eliminate the need for one or more time-consuming sample preparation steps while enabling fast coupling of SPME devices to the MS system (and fast desorption therefrom), with minimal alterations to the front-end of known systems, while nonetheless maintaining sensitivity, simplicity, selectivity, speed, and throughput. Moreover, in various aspects, the present teachings can enable a fully- or partially automated workflow, thereby further increasing throughput while potentially eliminating sources of human error in the analysis of SPME-derived samples. As discussed in detail below, methods and systems in accordance with various aspects of the present teachings provide sampling interfaces optimized so as to increase the sensitivity of the SPME-based workflow. In some aspects, for example, sampling interfaces in accordance with the present teachings can account for diverse geometries of known or hereafter-developed SPME devices (e.g., fibers, blades, micro-tips, pins, or mesh), while providing minimal dead volume about the sampling inlet of the ion source, thereby decreasing dilution and/or sample loss and improving instrument response and sensitivity. In some aspects, for example, the substrate-receiving port of the substrate sampling probe and the portion of the SPME substrate inserted therein can be configured such that the SPME substrate occupies at least 20 percent of the fluid volume in the substrate-receiving port (i.e., less than 80% of the volume of the substrate-receiving port is occupied by desorption solvent).

Figure 1:
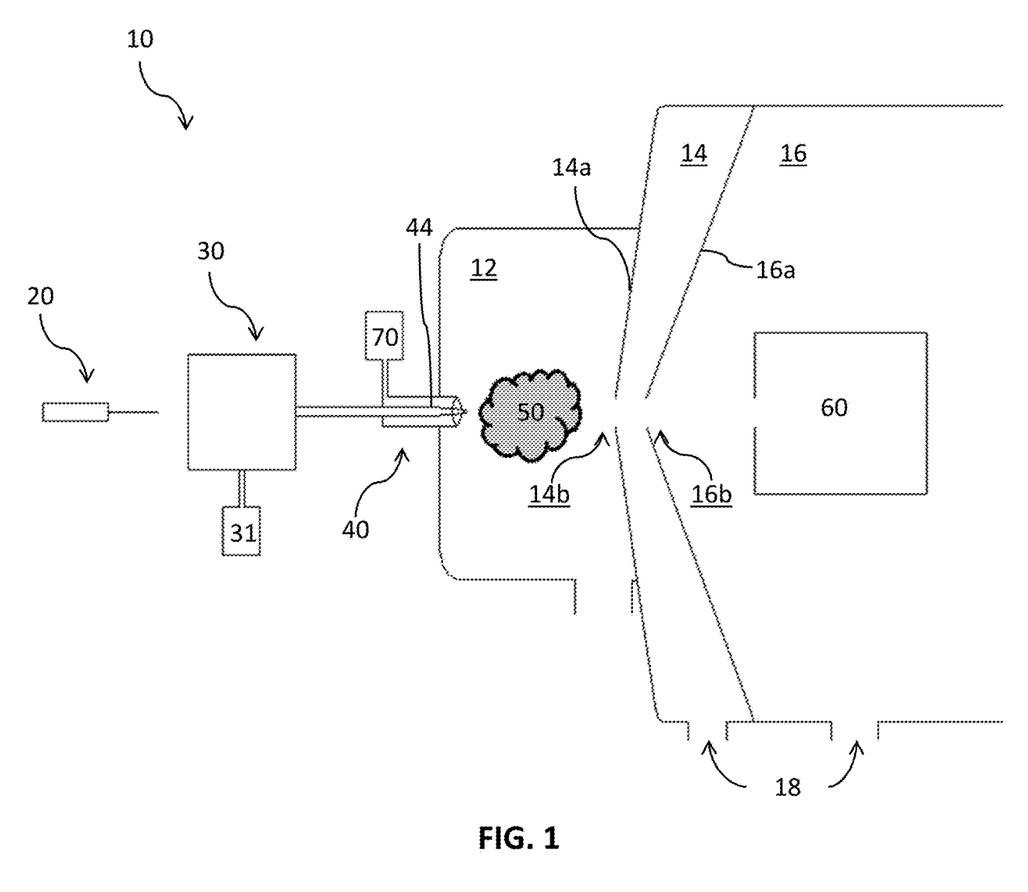
FIG. 1, in a schematic diagram, illustrates an exemplary system comprising a SPME substrate sampling interface fluidly coupled to an electrospray ion source of a mass spectrometer system in accordance with various aspects of the applicant's teachings.

FIG. 1 schematically depicts an embodiment of an exemplary system 10 in accordance with various aspects of the applicant's teachings for ionizing and mass analyzing SPME-extracted analytes. As shown in FIG. 1, the exemplary system 10 generally includes a substrate sampling probe 30 (e.g., an open port probe) in fluid communication with an ion source 40 for discharging a liquid containing one or more sample analytes into an ionization chamber 12, and a mass analyzer 60 in fluid communication with the ionization chamber 12 for downstream processing and/or detection of ions generated by the ion source. As will be discussed in more detail below, the substrate sampling probe 30 is generally configured to receive at least a portion of a substrate (e.g., SPME substrate 20) having a surface coated with an extraction phase to which one or more analytes from a sample are adsorbed and which is placed in a fluid pathway in the substrate sampling probe 30 extending between a desorption solvent source 31 and the ion source probe (e.g., electrospray electrode 44). In this manner, analytes desorbed from the coated surface of the SPME substrate 20 by the desorption solvent flow directly to the ion source 40 within the desorption solvent for ionization thereby.

In the depicted embodiment, the ionization chamber 12 can be maintained at an atmospheric pressure, though in some embodiments, the ionization chamber 12 can be evacuated to a pressure lower than atmospheric pressure. The ionization chamber 12, within which analytes desorbed from the SPME substrate 20 and contained in the desorption solvent that is discharged from the electrospray electrode 44 can be ionized, is separated from a gas curtain chamber 14 by a plate 14a having a curtain plate aperture 14b. As shown, a vacuum chamber 16, which houses the mass analyzer 60, is separated from the curtain chamber 14 by a plate 16a having a vacuum chamber sampling orifice 16b. The curtain chamber 14 and vacuum chamber 16 can be maintained at a selected pressure(s) (e.g., the same or different sub-atmospheric pressures, a pressure lower than the ionization chamber) by evacuation through one or more vacuum pump ports 18.

The ion source 40 can have a variety of configurations but is generally configured to generate analyte contained within a liquid (e.g., the desorption solvent) that is received from the substrate sampling probe 30. In the exemplary embodiment depicted in FIG. 1, an electrospray electrode 42, which can comprise a capillary fluidly coupled to the substrate sampling probe 20, terminates in an outlet end that at least partially extends into the ionization chamber 12 and discharges the desorption solvent therein. As will be appreciated by a person skilled in the art in light of the present teachings, the outlet end of the electrospray electrode 44 can atomize, aerosolize, nebulize, or otherwise discharge (e.g., spray with a nozzle) the desorption solvent into the ionization chamber 12 to form a sample plume 50 comprising a plurality of micro-droplets generally directed toward (e.g., in the vicinity of) the curtain plate aperture 14b and vacuum chamber sampling orifice 16b. As is known in the art, analytes contained within the micro-droplets can be ionized (i.e., charged) by the ion source 40, for example, as the sample plume 50 is generated. By way of non-limiting example, the outlet end of the electrospray electrode 44 can be made of a conductive material and electrically coupled to a pole of a voltage source (not shown), while the other pole of the voltage source can be grounded. Micro-droplets contained within the sample plume 50 can thus be charged by the voltage applied to the outlet end such that as the desorption solvent within the droplets evaporates during desolvation in the ionization chamber 12, bare charged analyte ions are released and drawn toward and through the apertures 14b, 16b and focused (e.g., via one or more ion lens) into the mass analyzer 60. Though the ion source probe is generally described herein as an electrospray electrode 44, it should be appreciated that any number of different ionization techniques known in the art for ionizing liquid samples and modified in accordance with the present teachings can be utilized as the ion source 40. By way of non-limiting example, the ion source 40 can be an electrospray ionization device, a nebulizer assisted electrospray device, a chemical ionization device, a nebulizer assisted atomization device, a photoionization device, a laser ionization device, a thermospray ionization device, or a sonic spray ionization device.

Figure 2:
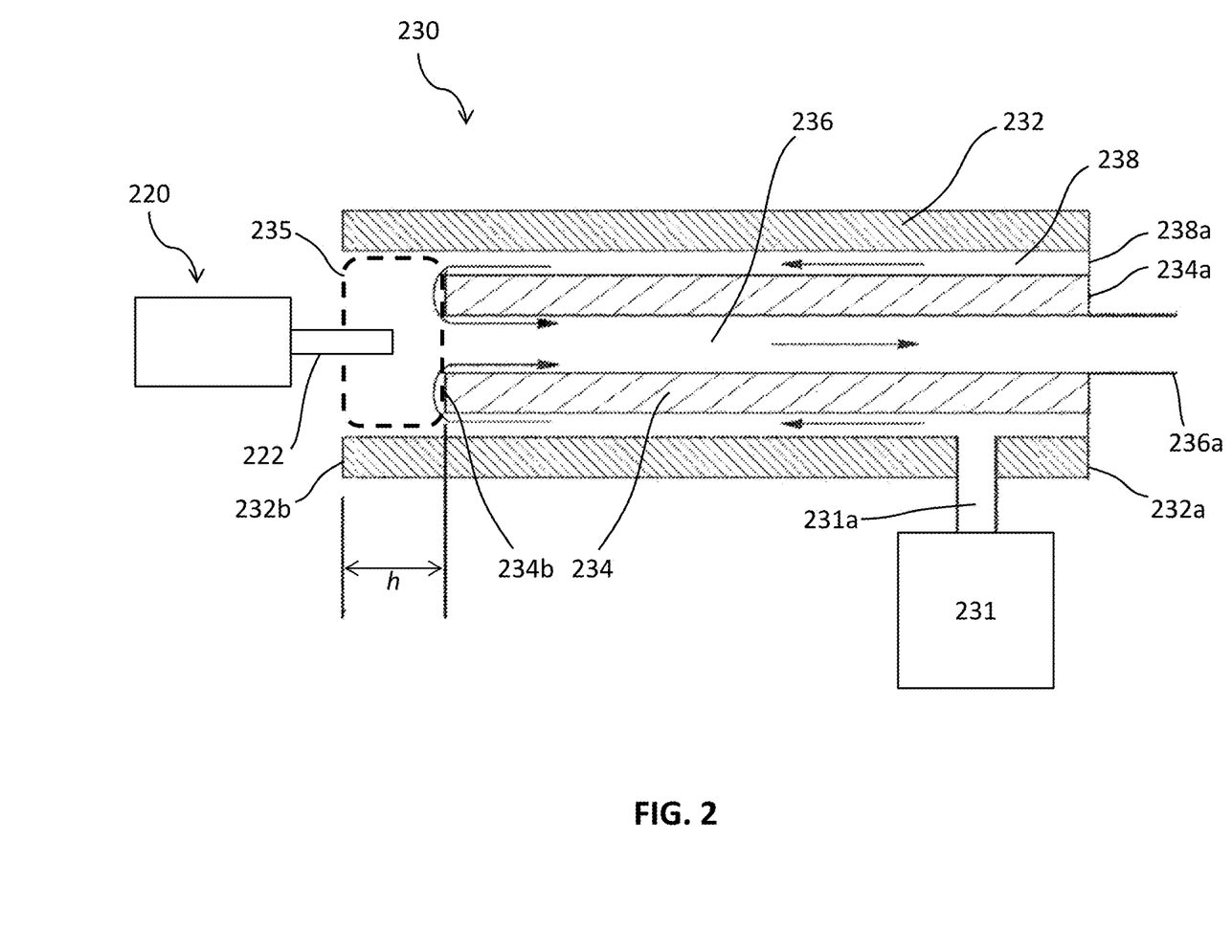
FIG. 2, in a schematic diagram, illustrates the exemplary substrate sampling interface of FIG. 1 in additional detail, in accordance with various aspects of the applicant's teachings.

With continued reference to FIG. 1, the mass spectrometer system 10 can optionally include a source 70 of pressurized gas (e.g. nitrogen, air, or noble gas) that supplies a high velocity nebulizing gas flow which surrounds the outlet end of the electrospray electrode 44 and interacts with the fluid discharged therefrom to enhance the formation of the sample plume 50 and the ion release within the plume for sampling by 14*b* and 16*b,* e.g., via the interaction of the high speed nebulizing flow and jet of liquid sample. The nebulizer gas can be supplied at a variety of flow rates, for example, in a range from about 0.1 L/min to about 20 L/min.

It will also be appreciated by a person skilled in the art and in light of the teachings herein that the mass analyzer 60 can have a variety of configurations. Generally, the mass analyzer 60 is configured to process (e.g., filter, sort, dissociate, detect, etc.) sample ions generated by the ion source 40. By way of non-limiting example, the mass analyzer 60 can be a triple quadrupole mass spectrometer, or any other mass analyzer known in the art and modified in accordance with the teachings herein. It will further be appreciated that any number of additional elements can be included in the mass spectrometer system including, for example, an ion mobility spectrometer (e.g., a differential mobility spectrometer) that is configured to separate ions based on their mobility through a drift gas rather than their mass-to-charge ratio. Additionally, it will be appreciated that the mass analyzer 60 can comprise a detector that can detect the ions which pass through the analyzer 60 and can, for example, supply a signal indicative of the number of ions per second that are detected.

With reference now to FIG. 2, an exemplary substrate sampling probe 230 (e.g., an open port probe) for desorbing one or more analytes from a SPME substrate 220 and suitable for use in the system of FIG. 1 is schematically depicted. As shown in FIG. 2, the substrate sampling probe 230 includes an outer tube (e.g., outer capillary tube 232) extending from a proximal end 232*a* to a distal end 232*b* and an inner tube (e.g., inner capillary tube 234) disposed co-axially within the outer capillary tube 232. As shown, the inner capillary tube 234 also extends from a proximal end 234*a* to a distal end 234*b*. The inner capillary tube 234 comprises an axial bore providing a fluid channel therethrough, which as shown in the exemplary embodiment of FIG. 2 defines a sampling conduit 236 through which liquid can be transmitted from the substrate sampling probe 230 to the ion source 40 of FIG. 1 (i.e., the sampling conduit 236 is fluidly coupled to inner bore of the electrospray electrode 44). On the other hand, the annular space between the inner surface of the outer capillary tube 232 and the outer surface of the inner capillary tube 234 can define a desorption solvent conduit 238 extending from an inlet end coupled to the desorption solvent source 231 (e.g., via conduit 231*a*) at a proximal end 238*a* to an outlet end (adjacent the distal end 234*b* of the inner capillary tube 234). In some exemplary aspects of the present teachings, the distal end 234*b* of the inner capillary tube 234 can be recessed relative to the distal end 232*b* of the outer capillary tube 232 (e.g., by a distance h as shown in FIG. 2) so as to define a distal fluid chamber 235 of the substrate sampling probe 230 that extends between and is defined by the distal end 234*b* of the inner capillary 234 and the distal end 232*b* of the outer capillary tube 232. Thus, the distal fluid chamber 235 represents the space adapted to contain fluid between the open distal end of the substrate sampling probe 230 and the distal end 234*b* of the inner capillary tube 234. Further, as indicated by the curved arrows of FIG. 2, the desorption solvent conduit 238 is in fluid communication with the sampling capillary 236 via this distal fluid chamber 235. In this manner and depending on the fluid flow rates of the respective channels, fluid that is delivered to the distal fluid chamber 235 through the desorption solvent conduit 238 can enter the inlet end of the sampling conduit 236 for transmission to its outlet end 236*a* and subsequently to the ion source. It should be appreciated that though the inner capillary tube 234 is described above and shown in FIG. 2 as defining the sampling conduit 236 and the annular space between the inner capillary tube 234 and the outer capillary tube 232 defines the desorption solvent conduit 238, the conduit defined by the inner capillary tube 234 can instead be coupled to the desorption solvent source 231 (so as to define the desorption solvent conduit) and the annular space defined between the inner and outer capillaries 234, 232 can be coupled to the ion source so as to define the sampling conduit.

As shown in FIG. 2, the desorption solvent source 231 can be fluidly coupled to the desorption solvent conduit 238 via a supply conduit 231*a* through which desorption solvent can be delivered from a reservoir of desorption solvent at a selected volumetric rate (e.g., via one or more pumping mechanisms including reciprocating pumps, positive displacement pumps such as rotary, gear, plunger, piston, peristaltic, diaphragm pump, and other pumps such as gravity, impulse and centrifugal pumps can be used to pump liquid sample), all by way of non-limiting example. Any desorption solvent effective to desorb analytes from the SPME device and amenable to the ionization process are suitable for use in the present teachings. Similarly, it will be appreciated that one or more pumping mechanisms can be provided for controlling the volumetric flow rate through the sampling conduit 236 and/or the electrospray electrode (not shown), these volumetric flow rates selected to be the same or different from one another and the volumetric flow rate of the desorption solvent through the desorption solvent conduit 238. In some aspects, these different volumetric flow rates through the various channels of the substrate sampling probe 230 and/or the electrospray electrode 244 can be independently adjusted (e.g., by adjusting the flow rate of the nebulizer gas) so as to control the movement of fluid throughout the system. By way of non-limiting example, the volumetric flow rate through the desorption solvent conduit 238 can be temporarily increased relative to the volumetric flow rate through the sampling conduit 236 (e.g., after withdrawal of a substrate) such that the fluid in the distal fluid chamber 235 overflows from the open end of the substrate sampling probe 230 to clean any residual sample deposited by the withdrawn substrate and/or to prevent any airborne material from being transmitted into the sampling conduit 236. In other aspects, the volumetric flow rates can be adjusted such that the fluid flow is decreased upon insertion of the substrate so as to concentrate the desorbed analytes in a smaller volume of desorption solvent.

In accordance with various aspects of the present teachings, at least a portion of the SPME substrate 220 can be inserted through the open end of the substrate sampling probe 230 such that the coated surface of the SPME substrate upon which one or more analyte species are adsorbed are disposed in the desorption solvent (e.g., the desorption solvent within the distal fluid chamber 235). As shown in FIG. 2, for example, the exemplary SPME substrate 220 comprises a coated surface 222 extending therefrom and upon which a SPME extraction phase (e.g., layer) has been formed and to which one or more analytes of interest have been adsorbed during extraction. Upon the coated surface 222 being inserted into the distal fluid chamber 235, the desorption solvent flowing from the desorption solvent conduit 238 and into the sampling conduit 236 via the distal fluid chamber 235 can be effective to desorb at least a portion of the one or more analytes adsorbed on the coated surface 222 such that the desorbed analytes flow with the desorption solvent into the inlet of the sampling conduit 236. SPME substrates for use in systems and methods in accordance with the present teachings are generally able to be at least partially inserted into a fluid pathway provided by a substrate sampling probe 230 such that the desorption solvent provided thereby is effective to desorb one or more analytes of interest from the SPME substrate, though the substrate configuration (e.g., fibers, blades, micro-tips, pins, or mesh) and/or SPME coating (e.g., HLB-PAN, C18-PAN, antibodies, etc.) is not particularly limited. Indeed, any known SPME substrate and coating chemistries known in the art or hereafter developed and modified in accordance with the present teachings can be used in the methods and systems disclosed herein. Exemplary SPME devices suitable for use in accordance with various aspects of the present teachings are described, for example, in U.S. Pat. No. 5,691,205, entitled "Method and Devise for Solid Phase Microextraction and Desorption" and PCT Pub. No. WO2015188282 entitled "A Probe for Extraction of Molecules of Interest from a Sample," the teachings of which are hereby incorporated by reference in their entireties.

It will be appreciated that substrate sampling probes in accordance with the present teachings can have a variety of configuration and sizes, with the depiction of substrate sampling probe 230 of FIG. 2 representing an exemplary depiction. By way of non-limiting example, the dimensions of an inner diameter of the inner capillary tube 234 can be in a range from about 1 micron to about 1 mm (e.g., 200 microns), with exemplary dimensions of the outer diameter of the inner capillary tube 234 being in a range from about 100 microns to about 3 or 4 centimeters (e.g., 360 microns). Also by way of example, the dimensions of the inner diameter of the outer capillary tube 232 can be in a range from about 100 microns to about 3 or 4 centimeters (e.g., 450 microns), with the typical dimensions of the outer diameter of the outer capillary tube 232 being in a range from about 150 microns to about 3 or 4 centimeters (e.g., 950 microns). The cross-sectional shapes of the inner capillary tube 234 and/or the outer capillary tube 232 can be circular, elliptical, superelliptical (i.e., shaped like a superellipse), or even polygonal (e.g., square). Moreover, as discussed in detail below, the inner diameter (or cross-sectional area) of the inner or outer capillary tubes 234, 232 need not be constant along the length of the capillary, but can instead include at least a portion having a relatively reduced diameter or cross-sectional area relative to other portions of the same inner or outer capillary tube 234, 232 in accordance with various aspects of the present teachings. In some other aspects, the cross-sectional area or a diameter of a portion of the distal fluid chamber 235 can be larger than an internal cross-sectional area or diameter of a proximal portion of the outer capillary tube 232, so as to enable the distal end 232b of the outer capillary tube 232 to receive an SPME device having at least one dimension larger relative the diameter of the proximal portion of the outer capillary tube (e.g., an SPME blade having a width greater than about 2 mm). Additional details regarding SPME sampling probes suitable for use in the system of FIG. 1 and modified in accordance with the present teachings can be found, for example, in U.S. Pub. No. 20130294971 entitled "Surface Sampling Concentration and Reaction Probe" and U.S. Pub. No. 20140216177 entitled "Method and System for formation and Withdrawal of a Sample From a Surface to be Analyzed" the teaching of which are hereby incorporated by reference in their entireties.

Figure 3A:
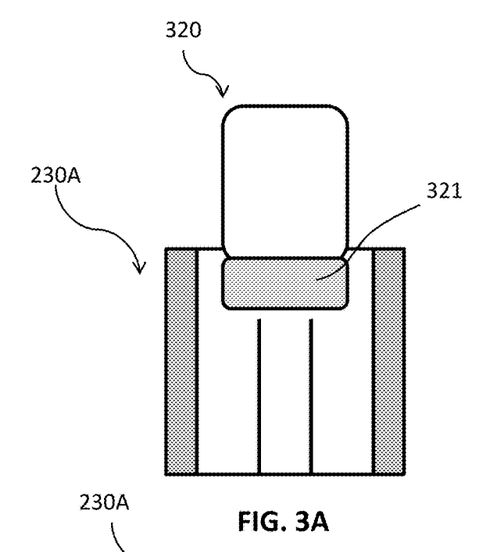
FIGS. 3A-G depict a SPME substrate inserted into an exemplary substrate sampling probes in accordance with various aspects of the present teachings.
Figure 3B:
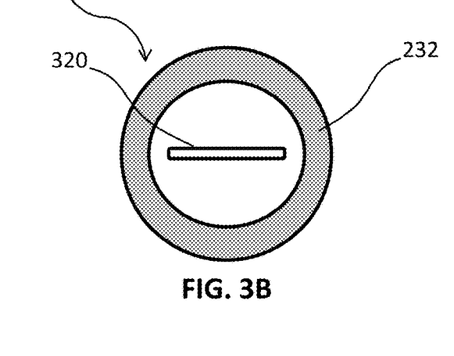
Figure 3C:
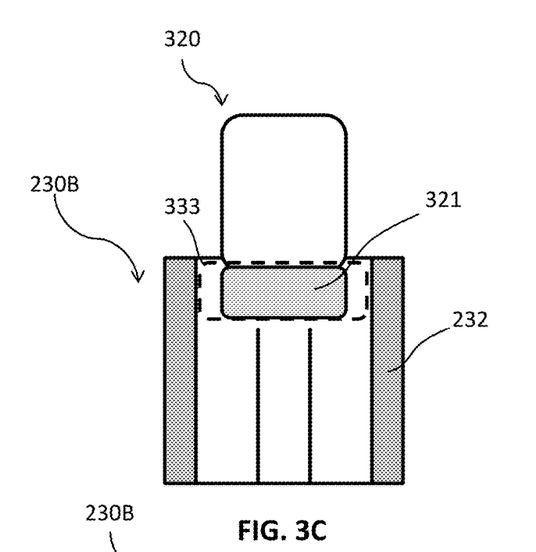
Figure 3D:
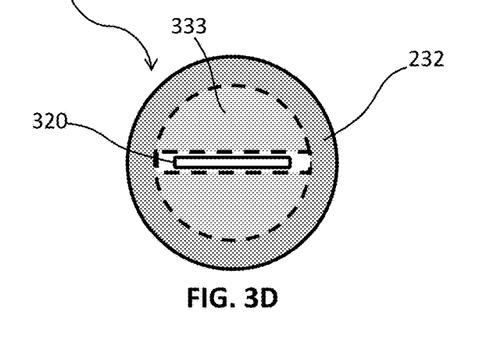

With reference now to FIG. 3A-G, an SPME substrate inserted into a substrate sampling probe in accordance with various aspects of the present teachings is depicted. First, as shown first in FIG. 3A and 3B, an exemplary SPME blade 320 having a coating 321 formed on each of the substantially planar surface about its distal end, as described, for example, PCT Pub. No. WO2015188282 entitled "A Probe for Extraction of Molecules of Interest from a Sample," the teachings of which are hereby incorporated by reference in its entirety, is depicted as being inserted into the open end of the substrate sampling probe 230A such that the coated area 321 is in contact with the desorption solvent as discussed otherwise herein. As best seen in the top view of FIG. 3B, however, the blade 320 takes up only a minor portion (e.g., less than 10%) of the volume of the distal fluid chamber of the substrate sampling probe 230A. Though analytes desorbed from the SPME blade 320 inserted into the substrate sampling probe 230A coupled to an ESI-MS system can be effective to provide sensitive detection of the target analytes without any LC sample preparation or purification step, it will be appreciated in light of the present teachings that the system of FIG. 3C and 3D can further optimize the detection of the target analytes by decreasing the dead volume of desorption fluid and increasing the concentration of the analytes therein. As shown in FIG. 3C and 3D, the distal end of the outer capillary tube 232 exhibits a reduced cross-sectional area relative to the device 230A depicted in FIGS. 3A and 3B, effectively reducing the total volume of the distal fluid chamber 235. Specifically, as shown in FIG. 3C and 3D, the inner sidewall of the outer capillary tube 232 extends radially so as to form a "plug" 333, which as shown has two opposed planar surfaces separated from one another by a distance greater than the thickness of the blade 320. In this manner, the volume of the distal fluid chamber is reduced in the substrate sampling probe 230B relative to that of the substrate sampling probe 230, thereby minimizing dilution of the desorbed analytes (e.g., via desorption into a greater volume of desorption solvent). It will also be appreciated in light of the present teachings that the "plug" 333 for reducing the volume of the distal fluid chamber 235 of probe 230B can be integral with the outer capillary tube 232 as shown in FIG. 3B (formed as an extension of the sidewall).

Figure 3E:
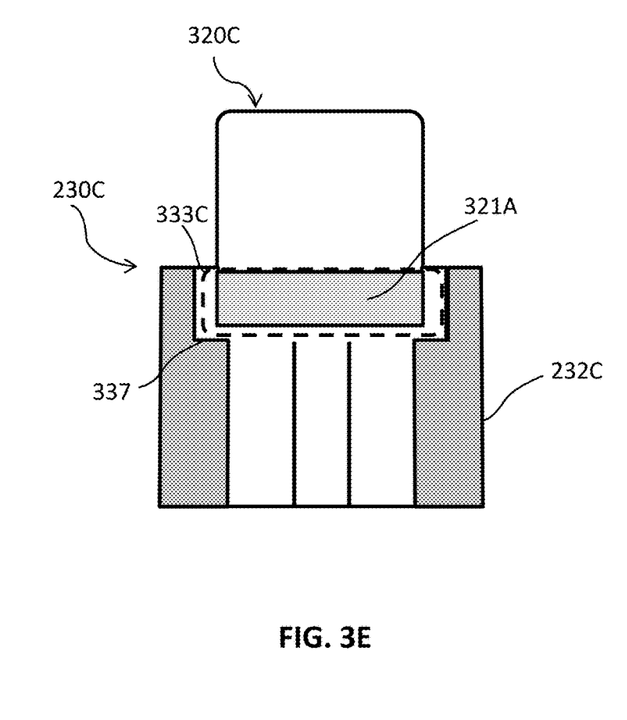
Figure 3F:
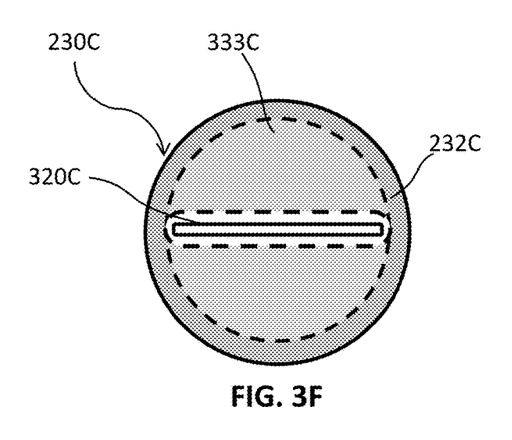
Figure 3G:
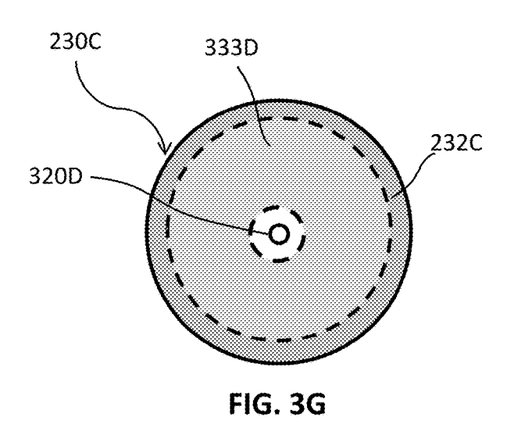

With reference now to FIGS. 3E and 3F another exemplary substrate sampling device 320C is depicted in which the distal end of the outer capillary tube 232C exhibits an increased cross-sectional area at its distal end so as to accommodate the insertion of blade 320C, for example, which exhibits a length greater than the internal diameter of the proximal portion of the device 230A, which has coated area 321A. As shown in FIG. 3E, the inner sidewall of the outer capillary tube defines a shoulder 337, upon which a plug 333C can be disposed, the plug 333C defining a passageway therethrough for receiving the blade 320C, and thereby reducing the total volume of the distal fluid chamber 235 despite the increase in the inner diameter of the distal portion of the outer capillary tube 232C. In various aspects, the plug 333 can be coupled to the distal end of the outer capillary tube 232C, for example, in a removable manner such that the volume of the distal fluid chamber of a substrate sampling probe 230C can be adjusted by coupling a particular plug according to the shape, size, or configuration of the SPME substrate used in a particular assay. As shown in FIG. 3G, for example, the plug 333D having a cylindrical orifice extending therethrough can be coupled to the distal end of the substrate sampling probe 230C for insertion of a cylindrical SPME fiber 320D. In some aspects, a kit can be provided comprising an SPME substrate and one or more plugs configured to couple to the open, distal end of the substrate sampling probe so as to minimize the volume of desorption fluid surrounding the SPME substrate when inserted into the plugged substrate sampling probe. Thus, in some aspects, sampling interfaces in accordance with the present teachings can account for diverse geometries of known or hereafter-developed SPME devices (e.g., fibers, blades, micro-tips, pins, or mesh), while providing minimal dead volume about the sampling inlet of the ion source, thereby decreasing dilution and/or sample loss and improving instrument response and sensitivity. In some aspects, for example, the substrate-receiving port of the substrate sampling probe can be configured such that the SPME substrate occupies at least 20 percent of the fluid volume in the substrate-receiving port (i.e., less than 80% of the volume of the substrate-receiving port is occupied by desorption solvent).

Figure 4:
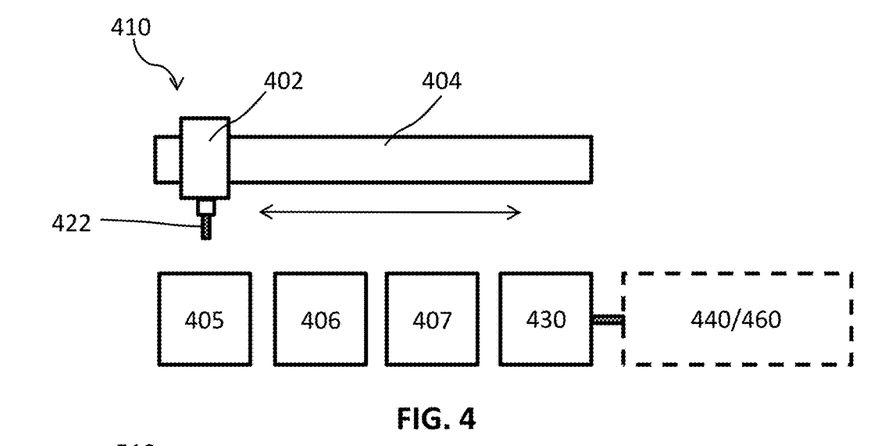
FIG. 4 depicts in schematic diagram an exemplary automated system for sample analysis in accordance with various aspects of the applicant's present teachings.
Figure 5:
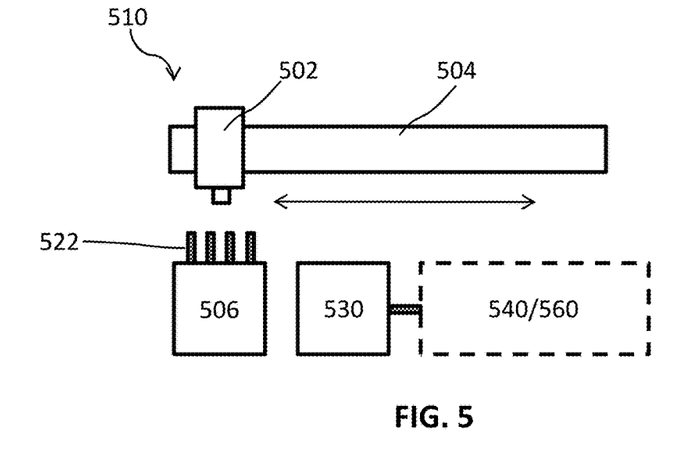
FIG. 5 depicts in schematic diagram another exemplary automated system for sample analysis in accordance with various aspects of the applicant's present teachings.

With reference now to FIG. 4, an exemplary automated sample analysis system 410 in accordance with various aspects of the present teachings is depicted. As shown in FIG. 5 and discussed otherwise herein, the present teachings reduce and/or eliminate the need for complex and time-consuming sample preparation steps such as liquid chromatography, thus enabling SPME-MS analysis in an automated fashion. As shown, the exemplary system 410 includes an actuation mechanism 404 (e.g., robotic arm, stage, electro-mechanical translator, step motor, etc.) that is coupled to a sample holder 402 configured to grip, hold, or otherwise couple to a SPME substrate 422. One exemplary robotic system suitable for use in accordance with the present teachings is the Concept-96 autosampler marketed by PAS Technologies). Under the control of a controller (not shown) and without human intervention, for example, the actuation mechanism 404 can be configured to transfer the fiber 422 through the complete sample preparation workflow including, for example, conditioning the substrate in element 405 (e.g., coating or otherwise functionalizing the surface to enable extraction of an analyte of interest), extraction/enrichment of the analytes from the sample in element 406 (e.g., by immersing the coated surface in the sample, with or without vortexing), rinsing the extracted sample in element 407 (e.g., by immersing the SPME substrate having analytes adsorbed thereto in $H_2O$ so as to remove some interfering molecules, salts, proteins, etc.), and inserting the rinsed SPME substrate into the substrate sampling probe 430. As discussed otherwise herein, the substrate sampling probe 430 is configured to desorb the analytes from the SPME substrate utilizing the desorption solvent in flowing fluid contact with the coated portion of the SPME substrate and delivering the desorption solvent containing said desorbed analytes directly to the ion source 440/mass spectrometer system 460 for ionization/mass spectrometric analysis. In various aspects, the desorbing solvent can be pumped continuously through the substrate sampling probe 430, or alternatively, can be set in stand-by mode, for example, during the extraction step. It will also be appreciated that one or more of these steps can be excluded in an automated sample protocol. By way of non-limiting example, rather than perform on-line fiber conditioning and desorption with the system 410, these steps may be performed "off-line", for example in a remote location with the SPME substrate having analytes adsorbed thereto being sent to the laboratory for desorption and MS analysis.

With reference now to FIG. 5, another exemplary automated system 510 in accordance with various aspects of the present teachings is depicted. System 510 is similar to that depicted in FIG. 4 in that it in includes an actuation mechanism 504 and a sample holder 502, but differs in that the system 510 includes a specimen stage configured to support a plurality of SPME fibers 522. In such a system, for example, a controller (not shown) can sequentially transfer each of the SPME fibers to the substrate sampling probe 530 for desorbing the analyte therefrom and delivering the desorbed analytes directly to the ion source 540/mass spectrometer system 560 via fluidic coupling for ionization/mass spectrometric analysis. Additionally, as with system 410 of FIG. 4, the system 510 can utilize step-wise protocols (e.g. steps 506, or other steps such as 405, 406, etc.). Such steps can be achieved simultaneously for multiple SPME devices for high-throughput. It will be noted that like the system 510 of FIG. 5, the system of FIG. 4 can additionally include a specimen stage configured to support a plurality of SPME devices for the analysis of one or more different samples.

EXAMPLES

The applicant's teachings can be even more fully understood with reference to the following examples and data presented in FIGS. 6A-E and 7A-D. Other embodiments of the applicant's teachings will be apparent to those skilled in the art from consideration of the present specification and practice of the present teachings disclosed herein. It is intended that these examples be considered as exemplary only.

Example 1

Clenbuterol Analysis from Urine

Figure 6:
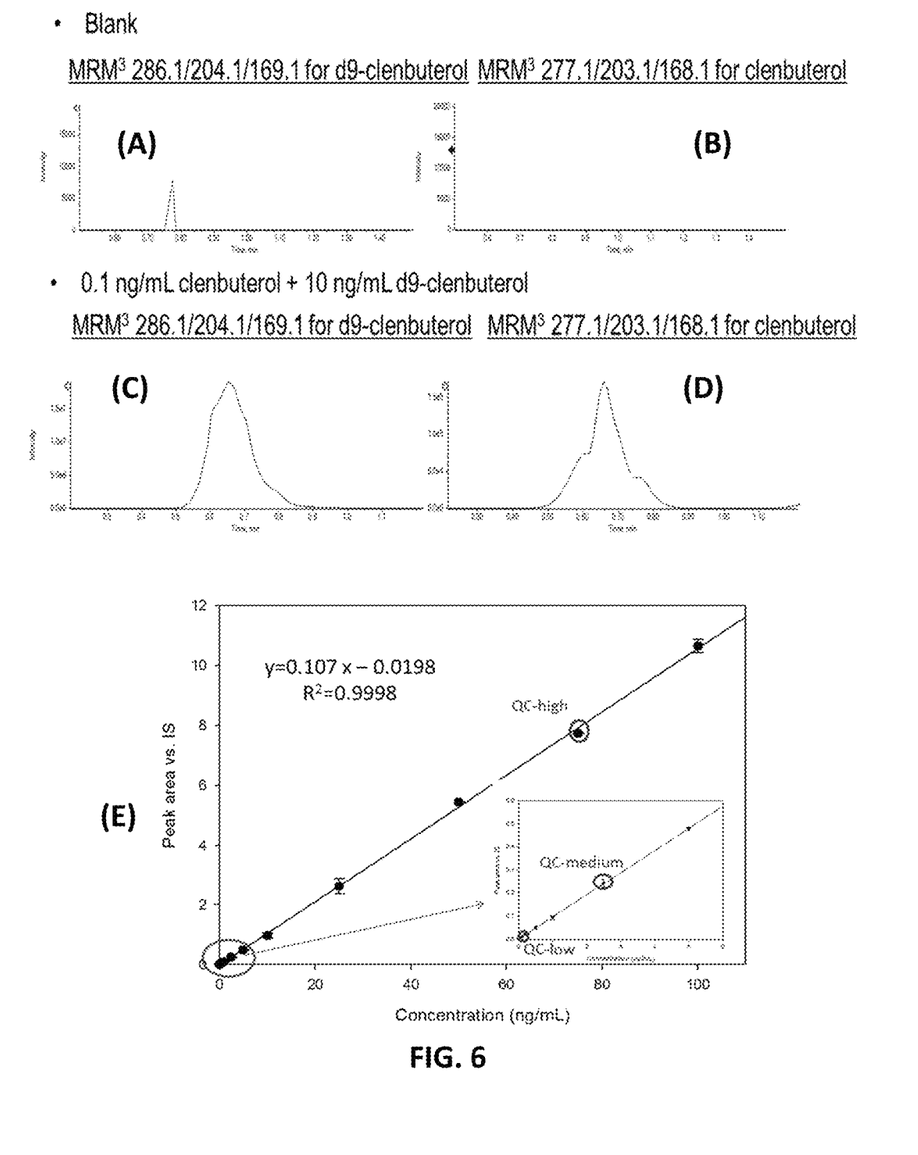
FIG. 6 depicts exemplary data for the SPME-based analysis of clenbuterol in human urine utilizing an exemplary system as depicted in FIG. 2 in accordance with various aspects of the applicant's present teachings.

Clenbuterol in urine was extracted with a C18-SCX coated SPME fiber (4 mm coating length, 0.045 mm coating thickness, 0.3 mm fiber diameter) by immersing the SPME fiber into 300 μL of urine spiked with 10 ng/mL d9-clenbuterol (as an internal standard) and clenbuterol with the concentration in a range from 0.1 to 100 ng/mL. The SPME fiber was immersed for 2 min under vortex mixing condition (1000 rpm). After extraction, the fiber was rinsed with water for 5 seconds, then inserted through the open upper end of a vertically-aligned, co-axial substrate sampling probe as depicted in FIG. 2 into a continuously flowing desorption solvent stream (pure methanol at a flow rate of 50 μL/min) for 5 seconds to desorb the analyte from the SPME fiber. The desorption solvent was transferred to the pneumatically assisted ESI electrode (TurboV ion source, SCIEX) coupled to a Qtrap 6500+ mass spectrometer (SCIEX) operated in $MRM^3$ mode (286.1/204.1/169.1 for d9-clenbuterol detection, and 277.1/203.1/168.1 for clenbuterol analysis). Total analysis time between sampling and signal was about 10 seconds. FIGS. 6A-D depict total ion intensity at the $MRM^3$ transitions for each of the sample. In $MRM^3$, $1^{st}$ fragment ions are trapped in Q3, followed by excitation to perform the $2^{nd}$ fragmentation step. The unique $2^{nd}$ generation product ions allow the differentiation of clenbuterol from interference. A calibration curve (FIG. 6E) was used to determine LOQ and linear dynamic range, with the x-axis as the clenbuterol concentration spiked in the urine sample, and the y-axis as the peak ratio of clenbuterol vs. d9-clenbueterol. Average and standard deviation (N=3) are plotted. The LOQ is shown to be <0.1 ng/mL.

Example 2

Codeine and Hydrocodone

Figure 7:
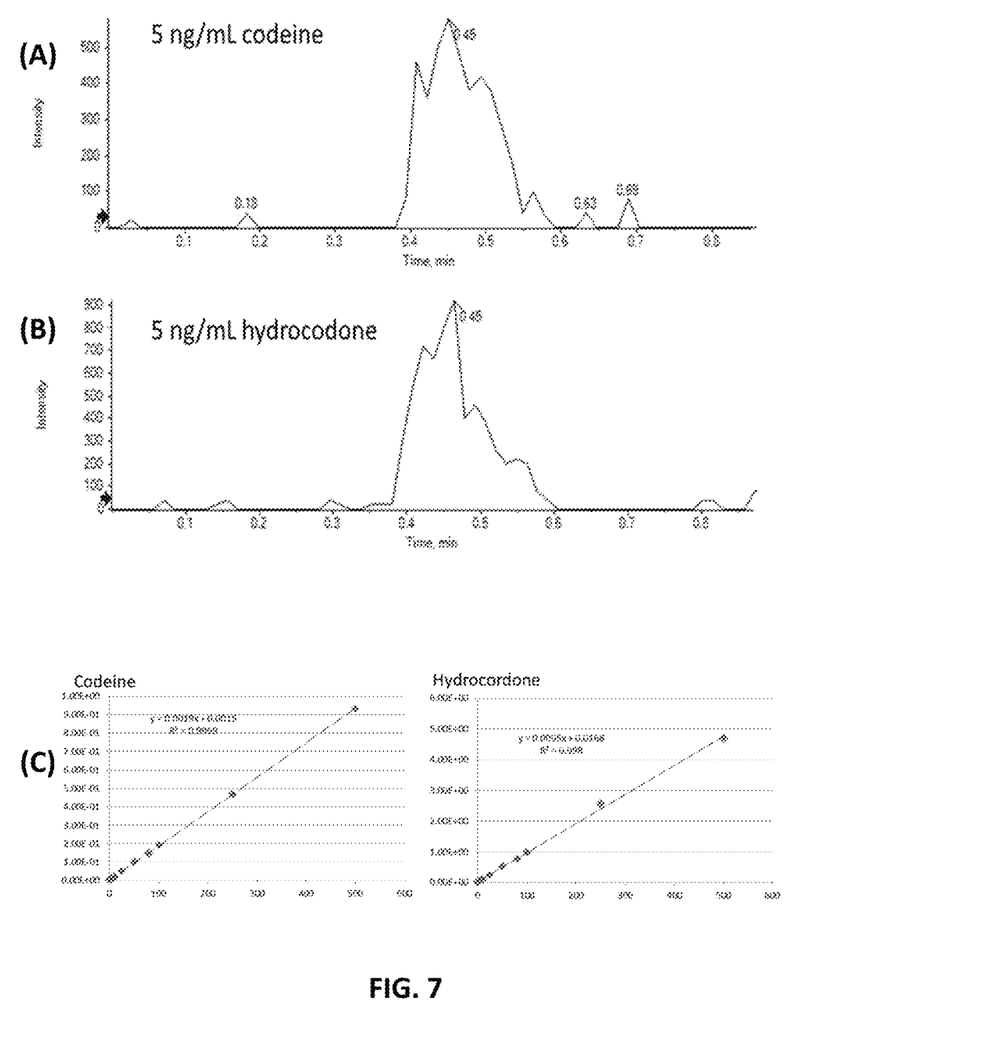
FIG. 7 depicts exemplary data for the SPME-based analysis of codeine and hydrocodone in human plasma utilizing an exemplary system as depicted in FIG. 2 in accordance with various aspects of the applicant's present teachings.

A mix-mode coated SPME fiber (C18-SCX particles, 4 mm coating length, 0.045 mm coating thickness, 0.3 mm fiber diameter) was immersed in 250 μL of plasma spiked with 100 ng d3-codeine (internal standard), d3-hydrocodone (internal standard), and various concentration of codeine and hydrocodone (from 1-500 ng/mL). The extraction time was 5 min (1000 rpm vortex) followed by a water rinse for 10 sec. The SPME fiber coating was inserted into the open port sampling interface for 5 seconds to transfer into the TurboV ion source (Sciex). Pure methanol was used as the desorption solvent in OPP, at the flow rate of 250 μL/min. The OPP and ion source were installed on a Qtrap 5500 system (SCIEX) equipped with a differential mobility spectrometer (DMS). As shown in FIGS. 7A-D, a detection limit of 1 ng/mL was achieved while a linear dynamic range up to 500 ng/mL was evaluated.

DMS is a gas-phase ion separation technique based on the mobility difference, with the DMS being placed between the ion source and the sampling orifice. In this study, DMS was used to differentiate codeine and hydrocodone and demonstrated good accuracy (>90%) and linearity ($R^2$>0.998) with the linear range of 0.1-100 ng/mL. It was also demonstrated that sampling with the SPME fiber could be performed remotely then shipped to a mass spectrometry lab for rapid automated analysis with an autosampler modified to insert the SPME fiber into the substrate sampling probe.

The section headings used herein are for organizational purposes only and are not to be construed as limiting. While the applicant's teachings are described in conjunction with various embodiments, it is not intended that the applicant's teachings be limited to such embodiments. On the contrary, the applicant's teachings encompass various alternatives, modifications, and equivalents, as will be appreciated by those of skill in the art.

The invention claimed is:

1. A system for analyzing a chemical composition of a specimen, comprising:
    a substrate sampling probe comprising:
    an outer capillary tube extending from a proximal end to a distal end; and
    an inner capillary tube extending from a proximal end to a distal end and disposed within said outer capillary tube, wherein said distal end of the inner capillary tube is recessed relative to the distal end of the outer capillary tube so as to define a distal fluid chamber between the distal end of the inner capillary tube and the distal end of the outer capillary tube,
    wherein said inner and outer capillary tubes define a desorption solvent conduit and a sampling conduit in fluid communication with one another via said distal fluid chamber, said desorption solvent conduit extending from an inlet end configured to fluidly couple to a desorption solvent source to an outlet end in fluid communication with said distal fluid chamber, and said sampling conduit extending from an inlet end in fluid communication with said distal fluid chamber to an outlet end configured to fluidly couple to an ion source probe for discharging desorption solvent received at the inlet end of the sampling conduit into an ionization chamber in fluid communication with a sampling orifice of a mass spectrometer,
    wherein the distal end of the outer capillary tube is configured to receive at least a portion of a substrate comprising a coated surface having one or more analyte species adsorbed thereto such that the coated surface is in contact with the desorption solvent as the desorption solvent flows from the desorption solvent conduit into the sampling conduit through the distal fluid chamber,
    and wherein a cross-sectional area of at least a portion of the distal fluid chamber is less than an internal cross-sectional area of a proximal portion of the outer capillary tube.

2. The system of claim 1, wherein said at least a portion of the substrate occupies at least 20 percent of said distal fluid chamber.

3. The system of claim 1, wherein the inner and outer capillary tubes are coaxial.

4. The system of claim 1, further comprising a plug configured to be coupled to the distal end of the outer capillary tube so as to reduce the volume of the distal fluid chamber.

5. The system of claim 1, wherein at least a portion of the distal fluid chamber comprises opposed planar surfaces, and wherein said substrate comprises a blade having a thickness less than a distance between said opposed planar surfaces.

6. The system of claim 1, wherein an axial bore of the inner capillary tube defines the sampling conduit and wherein a space between the inner capillary tube and the outer capillary tube defines the desorption solvent conduit.

7. The system of claim 1, wherein the substrate comprises a SPME substrate.

8. A system for performing chemical analysis, comprising:
    a substrate having a surface coated with an extraction phase configured to adsorb one or more species of analyte; and
    a substrate sampling probe comprising:
        an outer capillary tube extending from a proximal end to a distal end; and
        an inner capillary tube extending from a proximal end to a distal end and disposed within said outer capillary tube, wherein said distal end of the inner capillary tube is recessed relative to the distal end of the outer capillary tube so as to define a distal fluid chamber between the distal end of the inner capillary tube, an inner wall of the outer capillary tube, and the distal end of the outer capillary tube,
        wherein said inner and outer capillary tubes define a desorption solvent conduit and a sampling conduit in fluid communication with one another via said distal fluid chamber, said desorption solvent conduit extending from an inlet end configured to fluidly couple to a desorption solvent source to an outlet end in fluid communication with said distal fluid chamber, and said sampling conduit extending from an inlet end in fluid communication with said distal fluid chamber to an outlet end configured to fluidly couple to an ion source probe for discharging desorption solvent received at the inlet end of the sampling conduit into an ionization chamber in fluid communication with a sampling orifice of a mass spectrometer,
        wherein at least a portion of the substrate comprising the coated surface is configured to be inserted through the distal end of the outer capillary tube such that the coated surface having said analyte species adsorbed thereto is in contact with the desorption solvent as the desorption solvent flows from the desorption solvent conduit into the sampling conduit through the distal fluid chamber,
    and wherein a cross-sectional area of at least a portion of the distal fluid chamber is less than an internal cross-sectional area of a proximal portion of the outer capillary tube.

9. The system of claim 8, wherein said at least a portion of the substrate occupies at least 20 percent of said distal fluid chamber.

10. The system of claim 8, further comprising:
a desorption solvent source fluidly coupled to the inlet end of the desorption solvent conduit; and
a pump mechanism for delivering the desorption solvent from the desorption solvent source to the inlet end of the desorption solvent conduit.

11. The system of claim 10, further comprising an ion source probe, an ionization chamber, and a mass spectrometer system, wherein the ion source probe is in fluid communication with the outlet end of the sampling conduit and comprises a distal end disposed in the ionization chamber, wherein analytes contained within said desorption solvent are configured to ionize as the desorption solvent is discharged into the ionization chamber.

12. The system of claim 8, further comprising a specimen holder configured to support the substrate; and
an actuation mechanism coupled to the specimen holder and configured to insert the substrate into the distal end of the outer capillary tube such that the coated surface of said substrate is in contact with the desorption solvent.

13. The system of claim 8, wherein the substrate comprises a SPME substrate.

14. A method for performing chemical analysis, comprising:
inserting at least a portion of a SPME substrate into an open end of a substrate sampling probe, said SPME substrate having a surface coated with an extraction phase to which one or more analyte species are adsorbed, wherein inserting said SPME substrate comprises placing the coated surface having said one or more analytes species adsorbed thereto within a fluid pathway extending from a desorption solvent source to an ion source probe of an ion source;
flowing said desorption solvent through the fluid pathway such that at least a portion of said one or more analyte species is desorbed from the coated surface and is delivered to ion source probe within said desorption solvent;
discharging said desorption solvent containing said portion of the one or more analyte species from said ion source probe so as to ionize said one or more analyte species; and
performing mass spectrometric analysis on said one or more ionized analyte species,
wherein the substrate sampling probe comprises:
an outer capillary tube extending from a proximal end to a distal end; and
an inner capillary tube extending from a proximal end to a distal end and disposed within said outer capillary tube, wherein said distal end of the inner capillary tube is recessed relative to the distal end of the outer capillary tube so as to define a distal fluid chamber between the distal end of the inner capillary tube, an inner wall of the outer capillary tube, and the distal, open end of the outer capillary tube,
wherein said inner and outer capillary tubes define a desorption solvent conduit and a sampling conduit in fluid communication with one another via said distal fluid chamber, said desorption solvent conduit extending from an inlet end fluidly coupled to the desorption solvent source to an outlet end in fluid communication with said distal fluid chamber, and said sampling conduit extending from an inlet end in fluid communication with said distal fluid chamber to an outlet end fluidly coupled to the ion source probe,
and wherein a cross-sectional area of at least a portion of the distal fluid chamber is less than an internal cross-sectional area of a proximal portion of the outer capillary tube.

15. The method of claim 14, wherein inserting the portion of the SPME substrate into the open end of the substrate sampling probe comprises disposing the portion of the SPME substrate in the distal fluid chamber such that the SPME substrate occupies at least 30 percent of said distal fluid chamber.

16. The method of claim 14, further comprising inserting the SPME substrate into a sample so as to adsorb said one or more analyte species contained within the sample to the coated surface.

17. The method of claim 14, wherein performing mass spectrometric analysis comprises further comprising performing $MRM^3$ quantitation.

18. The method of claim 14, further comprising transmitting said one or more ionized analyte species through a differential mobility spectrometer prior to performing mass spectrometric analysis.

* * * * *